(12) United States Patent
Zandona' et al.

(10) Patent No.: US 9,913,663 B2
(45) Date of Patent: Mar. 13, 2018

(54) ANCHORING GROUP FOR AN EXTERNAL FIXATOR

(71) Applicant: ORTHOFIX S.R.L., Bussolengo (Verona) (IT)

(72) Inventors: Enrico Zandona', Verona (IT); Andrea Ottoboni, Rovigo (IT); Daniele Venturini, Povegliano Veronese (IT); Michele Coati, San Pietro in Cariano (IT)

(73) Assignee: Orthofix S.R.L., Verona (IT)

( * ) Notice: Subject to any disclaimer, the term of this patent is extended or adjusted under 35 U.S.C. 154(b) by 0 days.

(21) Appl. No.: 14/908,501

(22) PCT Filed: Jul. 10, 2014

(86) PCT No.: PCT/EP2014/001893
§ 371 (c)(1),
(2) Date: Jan. 28, 2016

(87) PCT Pub. No.: WO2015/014440
PCT Pub. Date: Feb. 5, 2015

(65) Prior Publication Data
US 2016/0157892 A1 Jun. 9, 2016

(30) Foreign Application Priority Data

Jul. 31, 2013 (EP) .................................... 13178833
Jul. 31, 2013 (EP) .................................... 13178834

(51) Int. Cl.
*A61B 17/56* (2006.01)
*A61B 17/64* (2006.01)

(52) U.S. Cl.
CPC ...... *A61B 17/6458* (2013.01); *A61B 17/6466* (2013.01)

(58) Field of Classification Search
CPC ..... A61B 17/66; A61B 17/62; A61B 17/6466; A61B 17/6416; A61B 17/6458;
(Continued)

(56) References Cited

U.S. PATENT DOCUMENTS 5,624,440 A * 4/1997 Huebner .............. A61B 17/645
606/54
6,217,577 B1 * 4/2001 Hofmann ........... A61B 17/6466
606/54

(Continued)

FOREIGN PATENT DOCUMENTS

WO         95/10240 A1    4/1995
WO      2014/111907 A1    7/2014

OTHER PUBLICATIONS

International Search Report, PCT/EP2014/001893, dated Oct. 20, 2014, 3 pages.
(Continued)

*Primary Examiner* — Eduardo C Robert
*Assistant Examiner* — Tara R Carter
(74) *Attorney, Agent, or Firm* — Baker & McKenzie LLP

(57) ABSTRACT

An anchoring group (20) for an external fixator (1), comprising: a connecting body (11) designed to be coupled to a bar (2) of an external fixator (1), said connecting body (11) being crossed by a median plane (M); a first locking device (10) for locking first unicortical pins and connected to the connecting body (11), said first locking device (10) comprising at least one seat; and a second locking device (10) for locking second unicortical pins and also connected to the connecting body (11), said second locking device (10) comprising at least one auxiliary seat, which is not aligned with the at least one seat of the first locking device (10), said first and second locking devices (10) extending from different side of said median plane (M), wherein the connecting body (11) has at least two fastening seats (110a, 110b) for
(Continued)

each the first and the second locking devices (10) so as to allow at least two alternative mounting configurations from each side with respect to the median plane (M) of the connecting body (11).

13 Claims, 18 Drawing Sheets

(58) Field of Classification Search
CPC . A61B 17/60; A61B 17/6425; A61B 17/6441; A61B 17/6433; A61B 17/6475
USPC .................................................... 606/53–59
See application file for complete search history.

(56) References Cited

U.S. PATENT DOCUMENTS

| 6,221,072 B1 * | 4/2001 | Termaten | A61B 17/6483 |
| | | | 606/54 |
| 2006/0229605 A1 * | 10/2006 | Olsen | A61B 17/6416 |
| | | | 606/54 |

OTHER PUBLICATIONS

Written Opinion of the International Searching Authority, PCT/EP2014/001893, dated Oct. 20, 2014, 5 pages.

* cited by examiner

ANCHORING GROUP FOR AN EXTERNAL FIXATOR

FIELD OF APPLICATION

The present invention is applicable in the field of orthopaedic surgery and relates in particular to an anchoring group for an external fixator, particularly suitable for the fixation of unicortical pins.

The invention also relates to an external fixator comprising said anchoring group.

PRIOR ART

External fixators are widely used for the treatment of bone fractures or for joining together two or more bone fragments. Known fixators comprise bone screws which are inserted in the bones and use external devices such as fixation clamps, fixation bars, rings, etc., that allow the creation of a rigid structure able to hold together the bone fragments in the desired position until completely healed.

These external fixators have the advantage of ensuring strength and stability owing, among other things, to the use of bone screws which penetrate into the bones at a sufficient depth; in particular, these screws pass through the bone cortex in two points so as to provide a flexurally resistant fastening.

However, the use of bi-cortical screws may be excessively invasive for patients in critical conditions, who for example have multiple fractures along with, in some case, extensive wounds and/or contusions. In particular the time devoted to checking the tip which emerges from the second cortex may be critical.

Also, with particular reference to the reduction of fractures in long bones, the aforementioned bi-cortical screws pass through the medullary cavity, which makes it impossible to simultaneously insert a medullary nail, which is particularly suitable for the treatment of certain types of trauma.

Moreover, the surgical implant of a definitive fixator of the aforementioned type requires time and suitable facilities and is not always compatible with the unforeseen circumstances where rapid intervention is required; for example, it is relatively difficult to perform the implant of such an external fixator in the context of a field hospital or in any case under environmental conditions where sterility is not guaranteed and where the fracture must be treated as a matter of emergency.

In order to meet these specific needs, external fixators of a provisional nature have been developed that, in addition to having a structure which is generally slimmer and lighter, use unicortical screws or unicortical pins for the attachment to the bone, i.e. that have been designed to be screwed in superficially so that they are attached to a single bone cortex only.

The unicortical pin undoubtedly represents a less invasive fixation system than conventional bone screws; moreover, owing to its limited penetration, the pin does not reach the medullary cavity of the bone, thus avoiding the risk of unwanted infections.

On the other hand, however, owing to its limited stability—due mainly to the fact that it passes through one cortex only, which means that flexural strength is limited—this type of screw is not widely used in external fixation applications.

It would instead be desirable to be able to use an external fixator, which has the advantages of stability and strength typical of provisional fixation systems, and to combine it with the advantages of ease of application, lightness and limited invasiveness that are instead typical of systems that use unicortical pins.

The technical problem forming the basis of the present invention is therefore to devise an anchoring group to be associated with external fixators, which is able to create a structure sufficiently rigid for it to withstand the external loads acting on it, so as to allow the formation of external fixators that are extremely flexible, but that at the same time have that degree of structural rigidity that typically distinguishes external fixation systems.

The device should have an optimum performance, under traction and compression, of the tip in the cortex of the bone and should eliminate, as far as possible, the flexural stresses acting on the shank of the single screw.

SUMMARY OF THE INVENTION

The aforementioned technical problem is solved by an anchoring group for an external fixator according to claim 1.

The technical problem is also solved by an external fixator comprising the anchoring group, according to what is stated in claim 14.

Owing to its form characteristics the anchoring group described above may be advantageously used on external fixators which ensures exceptional stability, in spite of the use of only unicortical pins. In fact the anchoring group makes it possible to obtain a closed reticular structure which provides a sought-after flexural and torsional stability.

Further features and advantages will become clearer from the detailed description provided below of a preferred, but not exclusive, embodiment of the present invention, with reference to the attached figures provided by way of non-limiting example.

DETAILED DESCRIPTION

Figure 1:
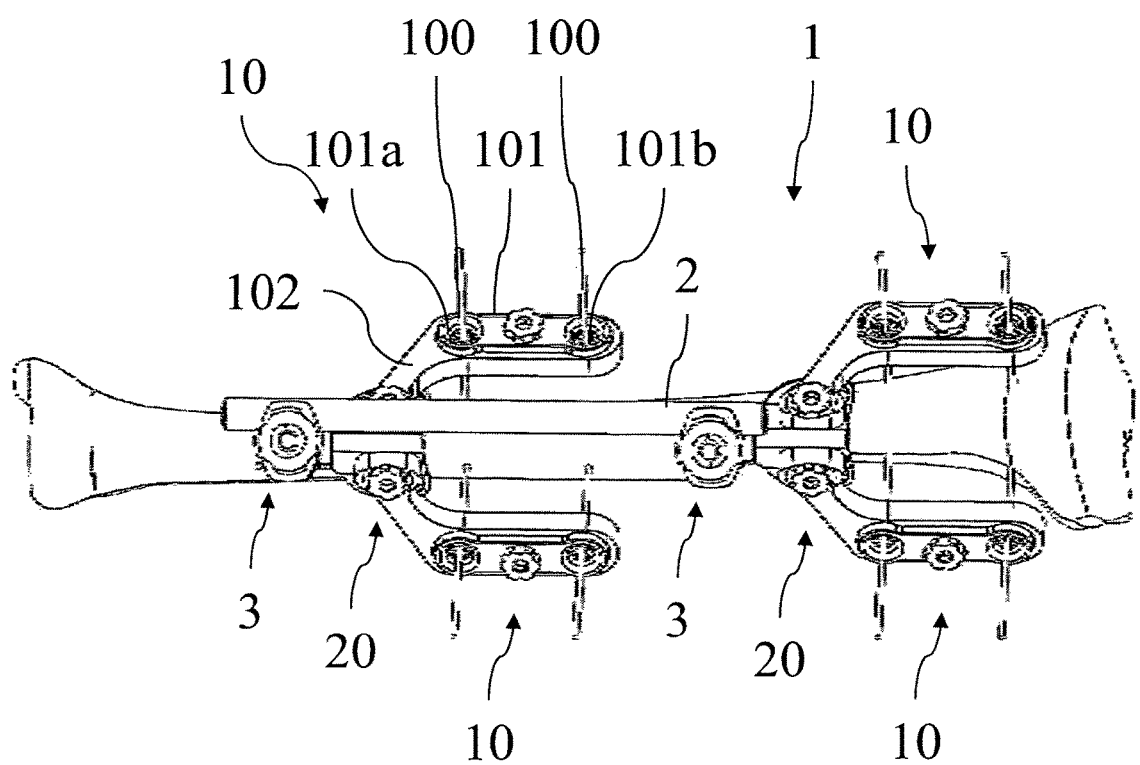
FIGS. 1-4 show different perspective views of an external fixator according to the present invention associated with the long bone of a patient, where locking devices of the distal and proximal anchoring groups are mounted in different configurations.
Figure 2:
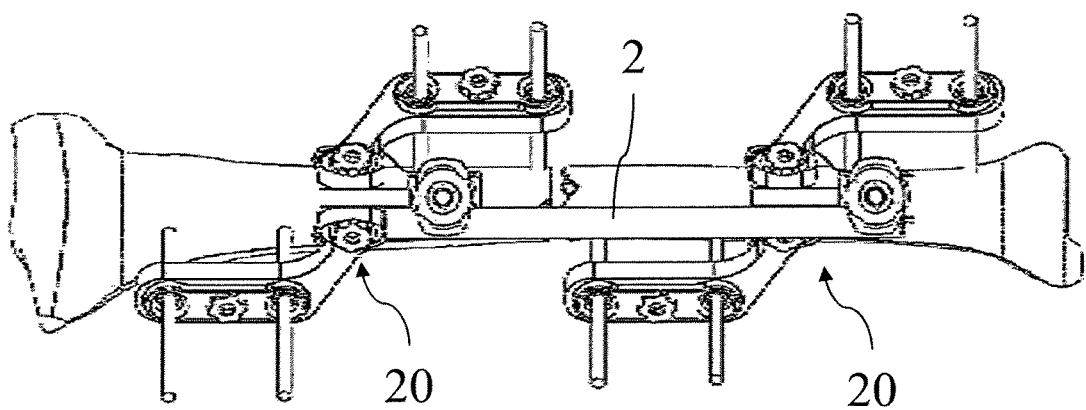
Figure 3:
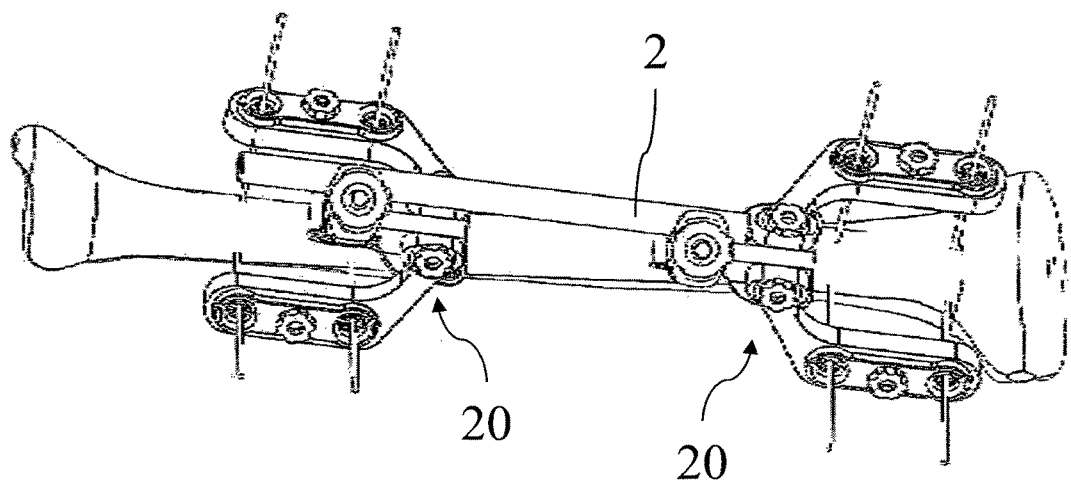
Figure 4:
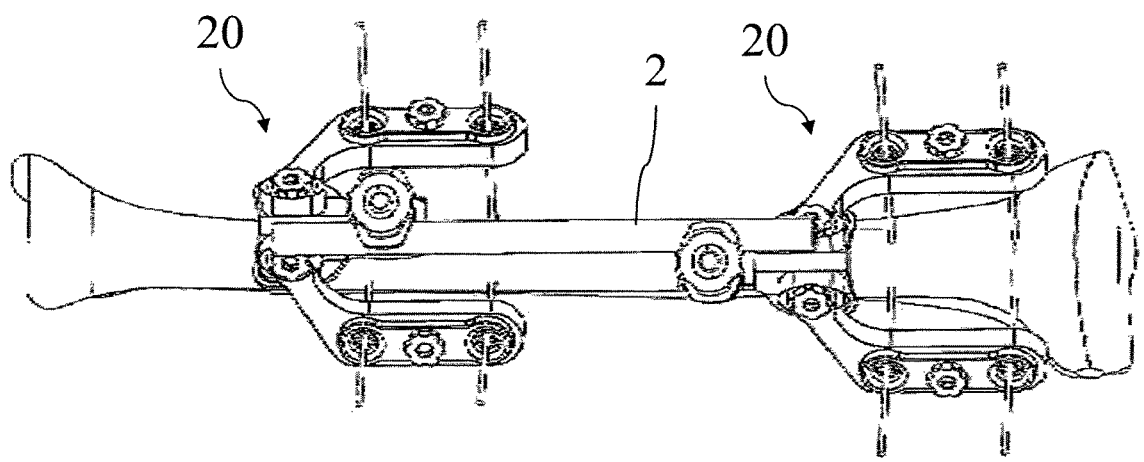
Figure 5:
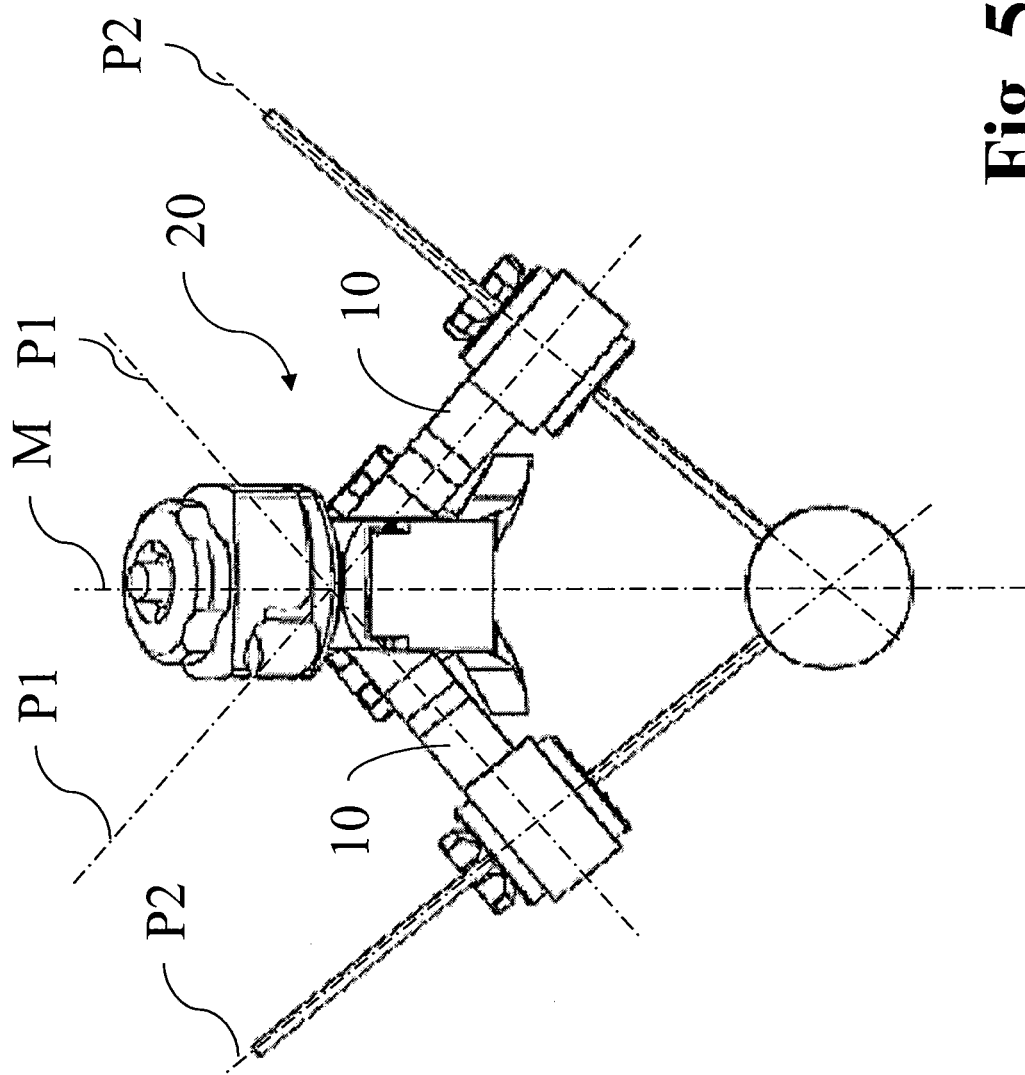
FIG. 5 shows a front view of an anchoring group according to the present invention associated with the bone of a patient.
Figure 6:
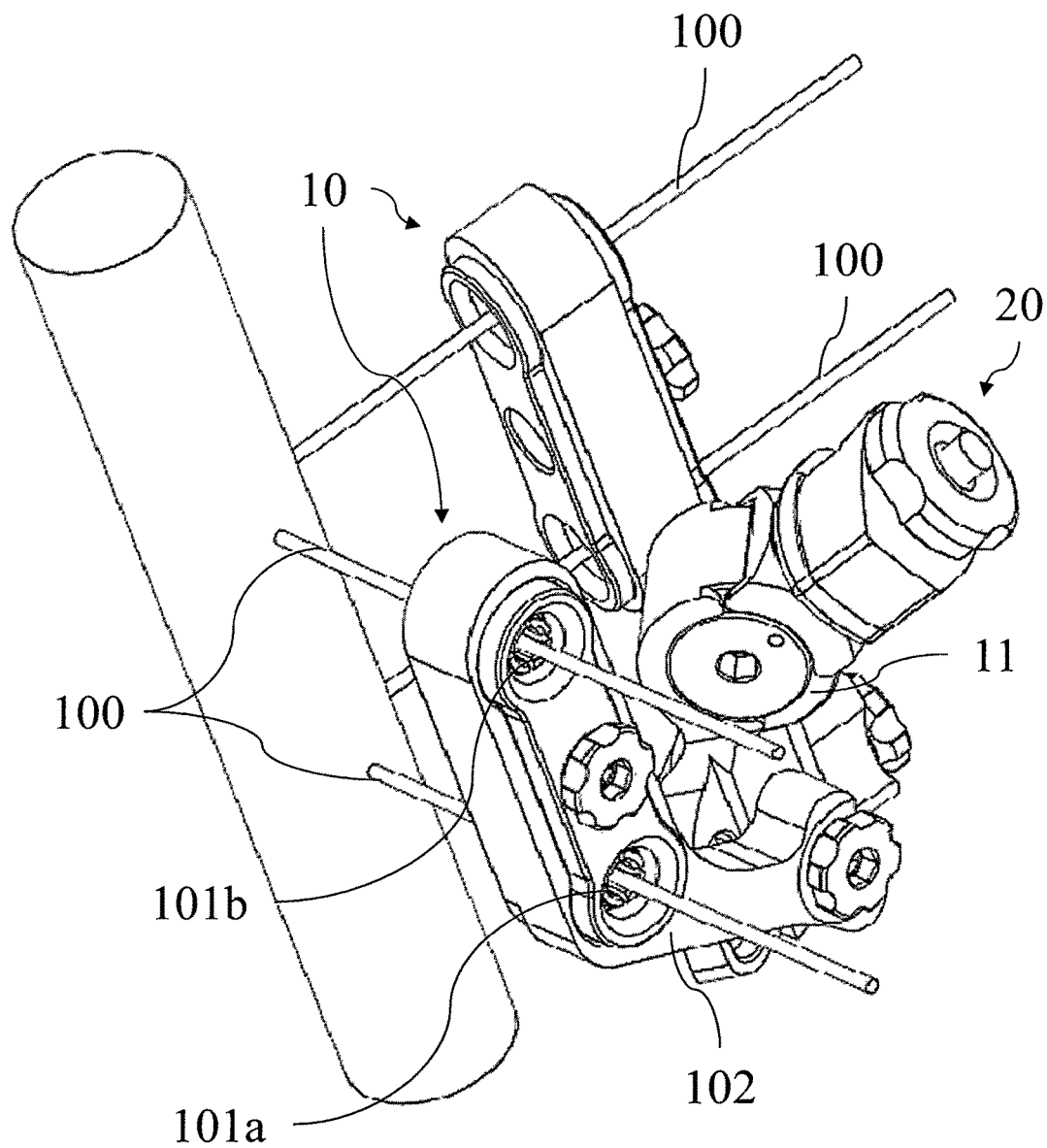
FIG. 6 shows a perspective view of the anchoring group of FIG. 5.
Figure 7:
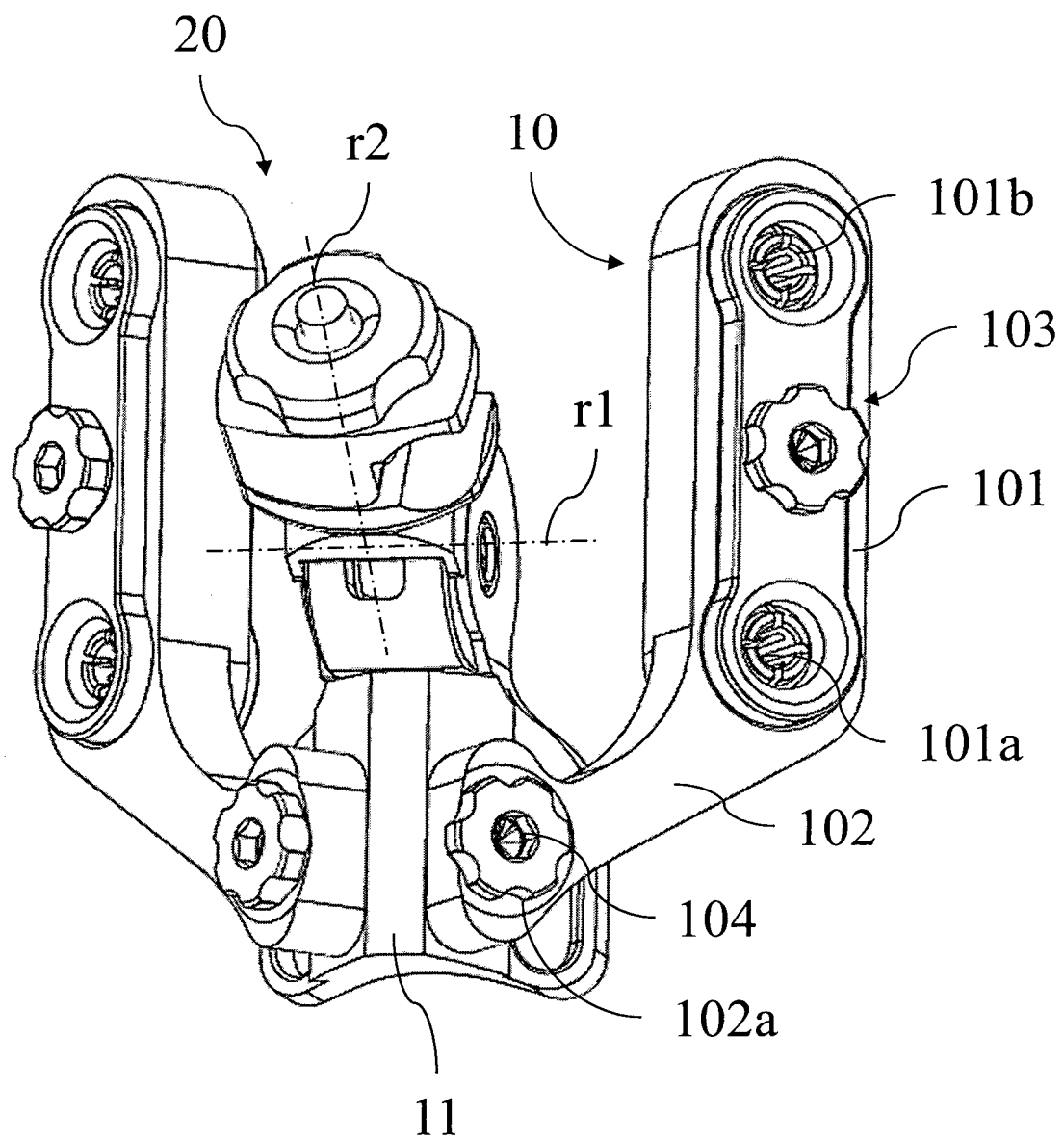
FIGS. 7 and 8 show two perspective views of the anchoring group according to the present invention, in which mounting of the locking devices in two different configurations is shown.
Figure 8:
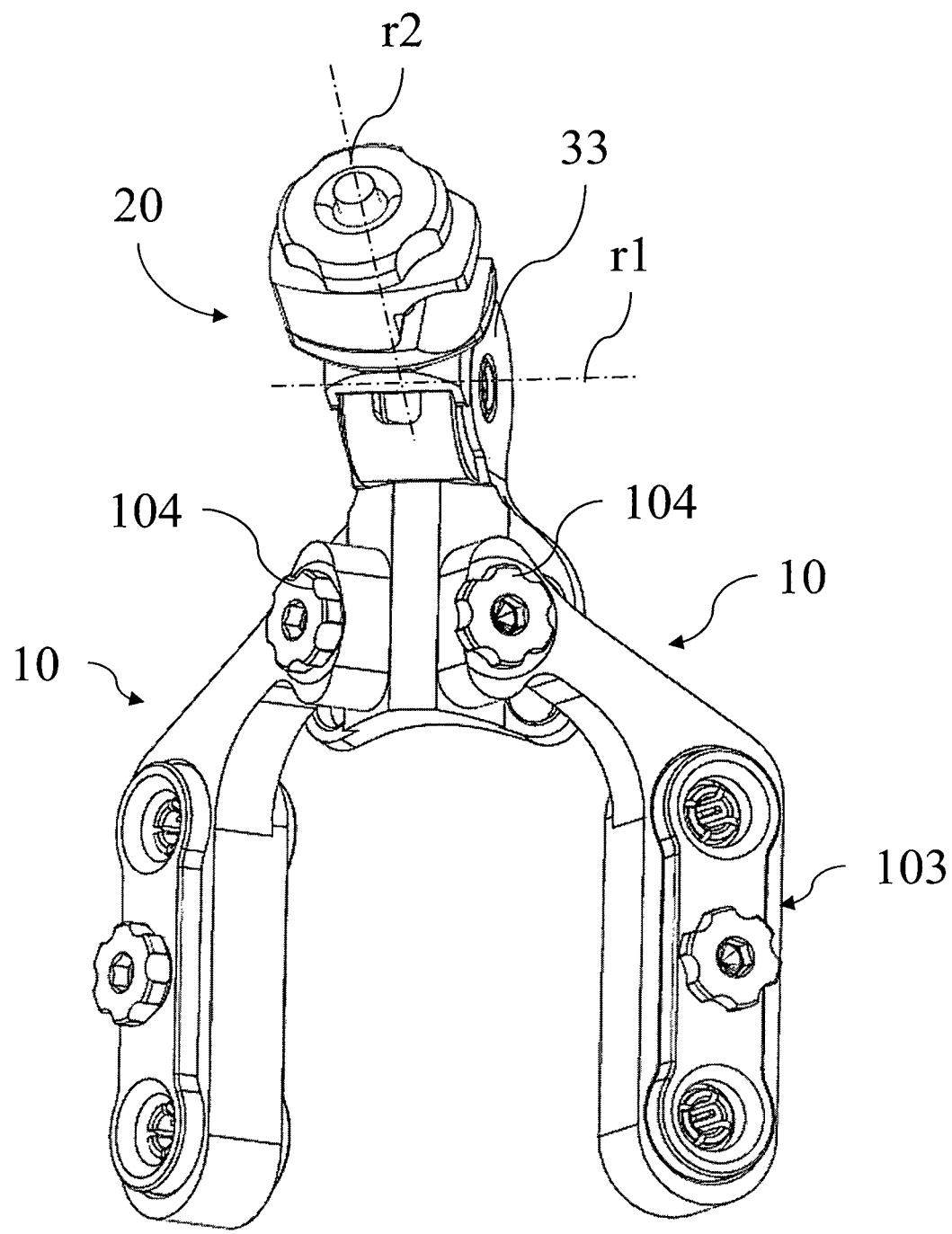
Figure 9:
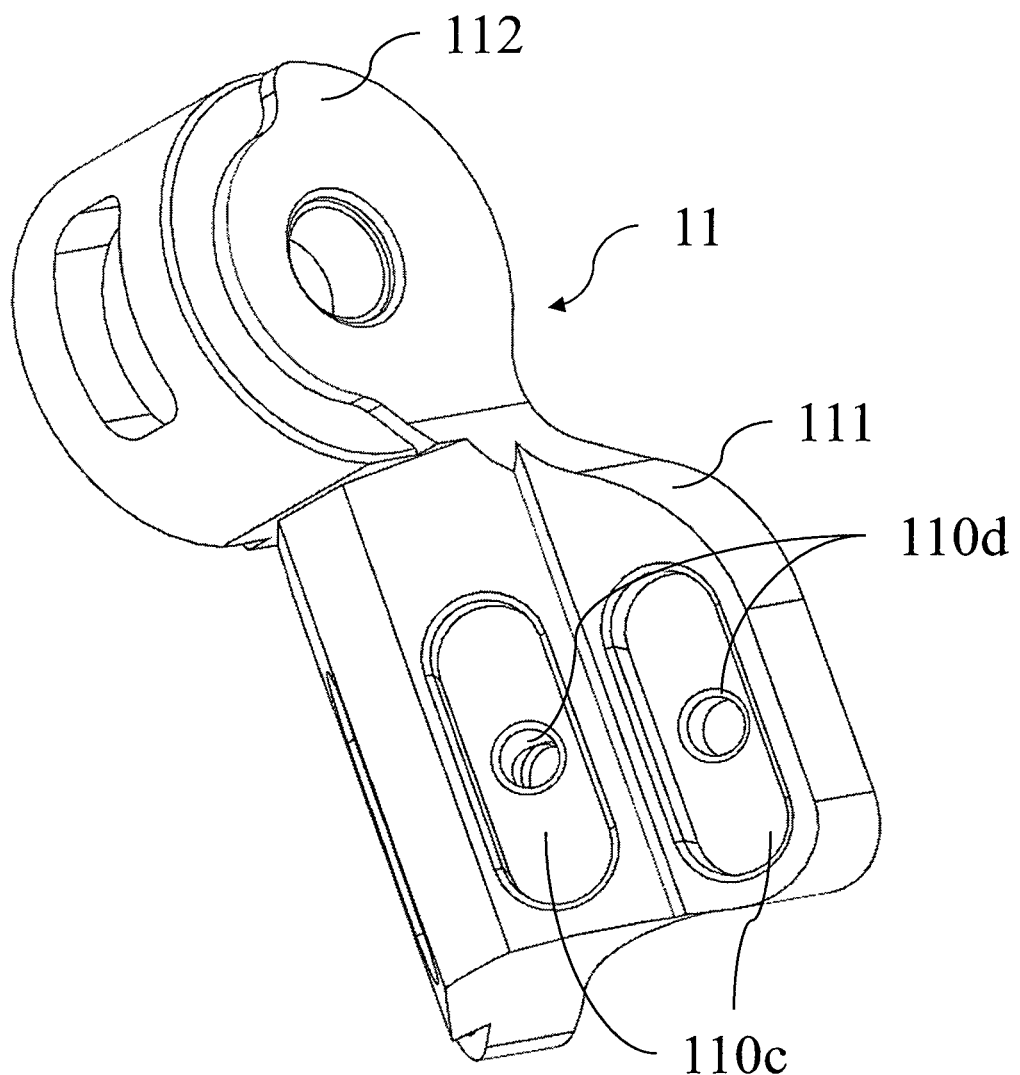
FIG. 9 shows a perspective view of a connecting body of the anchoring group according to the present invention.
Figure 10:
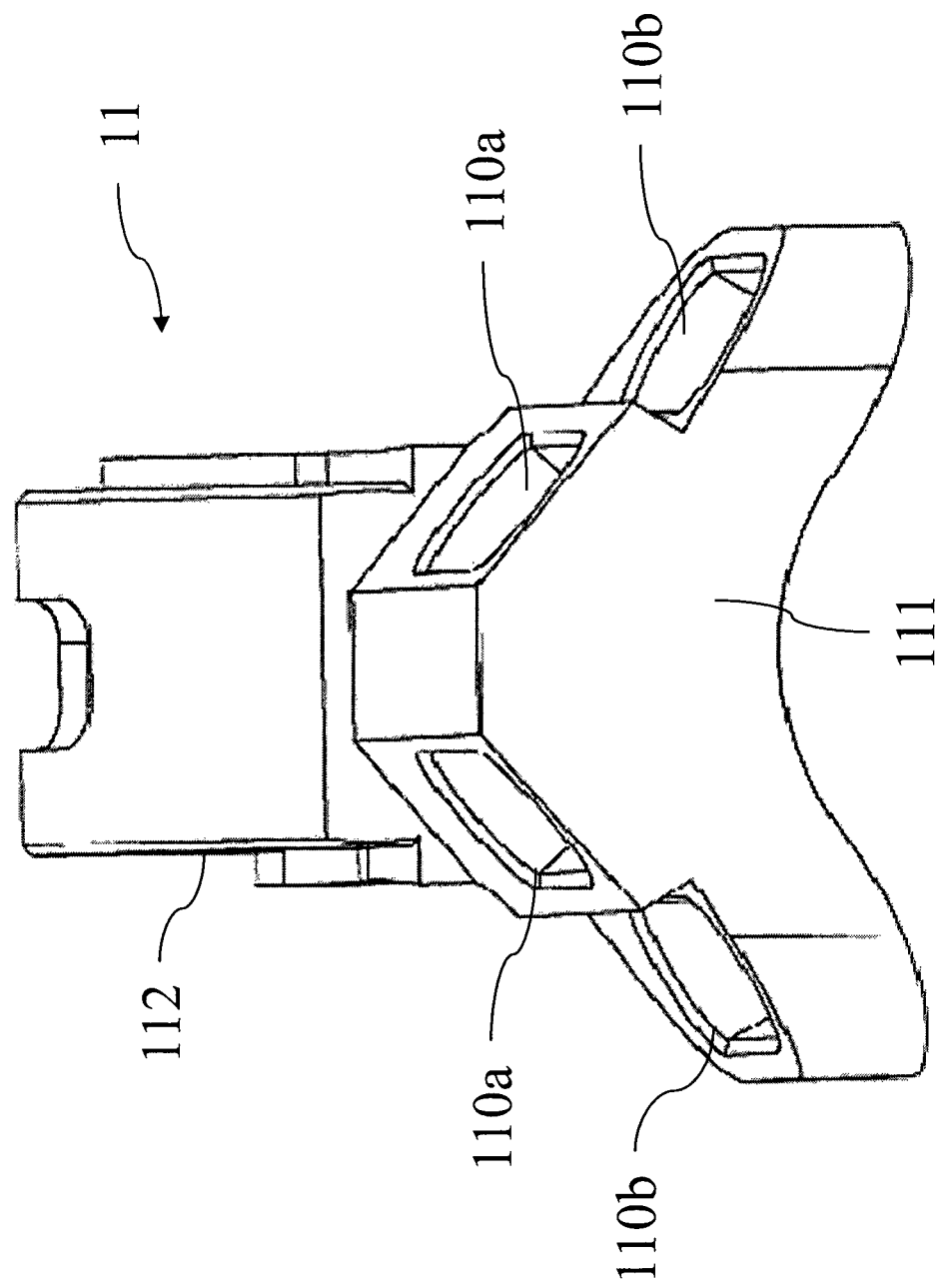
FIG. 10 shows a front view of the connecting body of FIG. 9.
Figure 11:
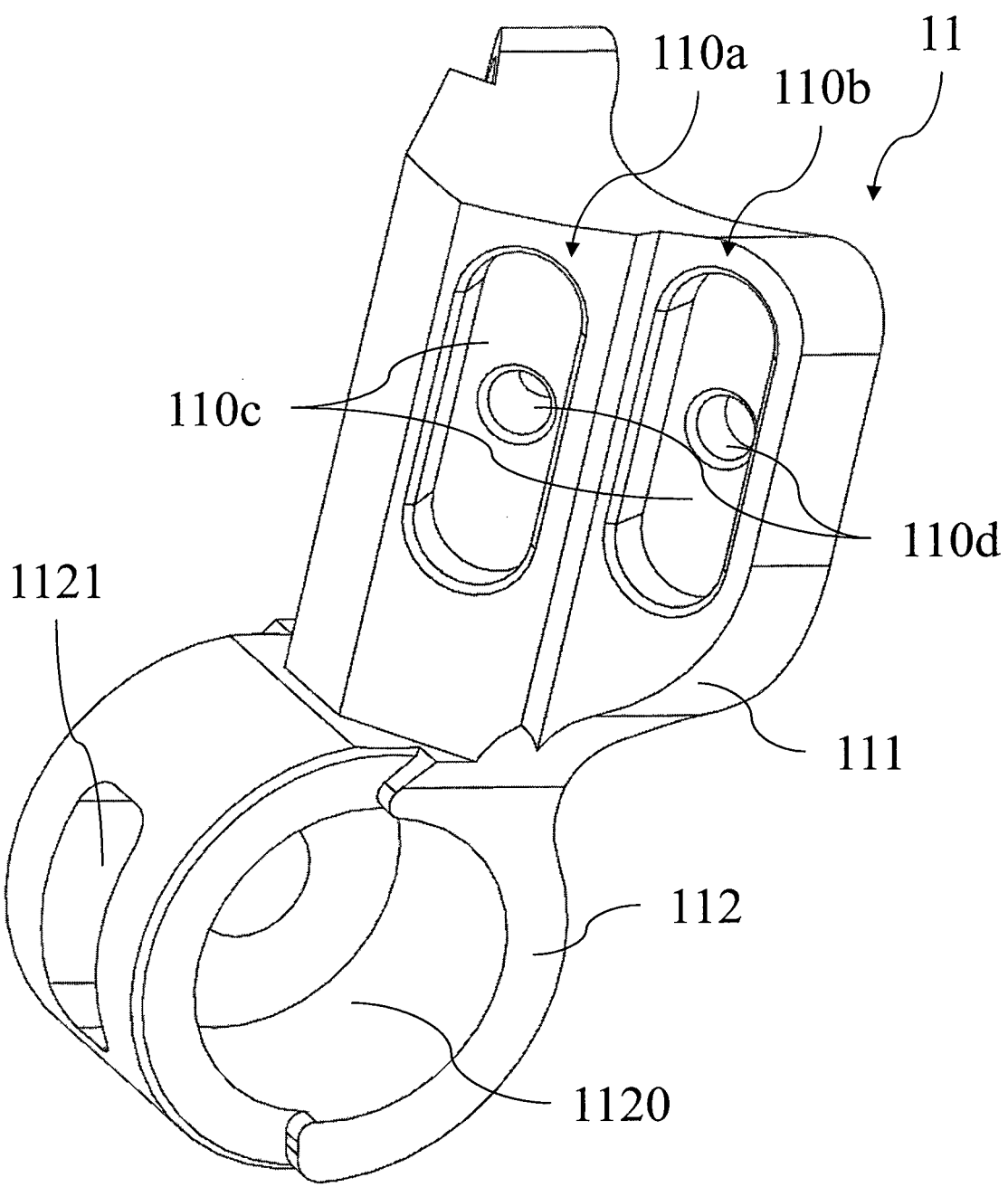
FIG. 11 shows a further perspective view of the connecting body of FIG. 9.
Figure 12:
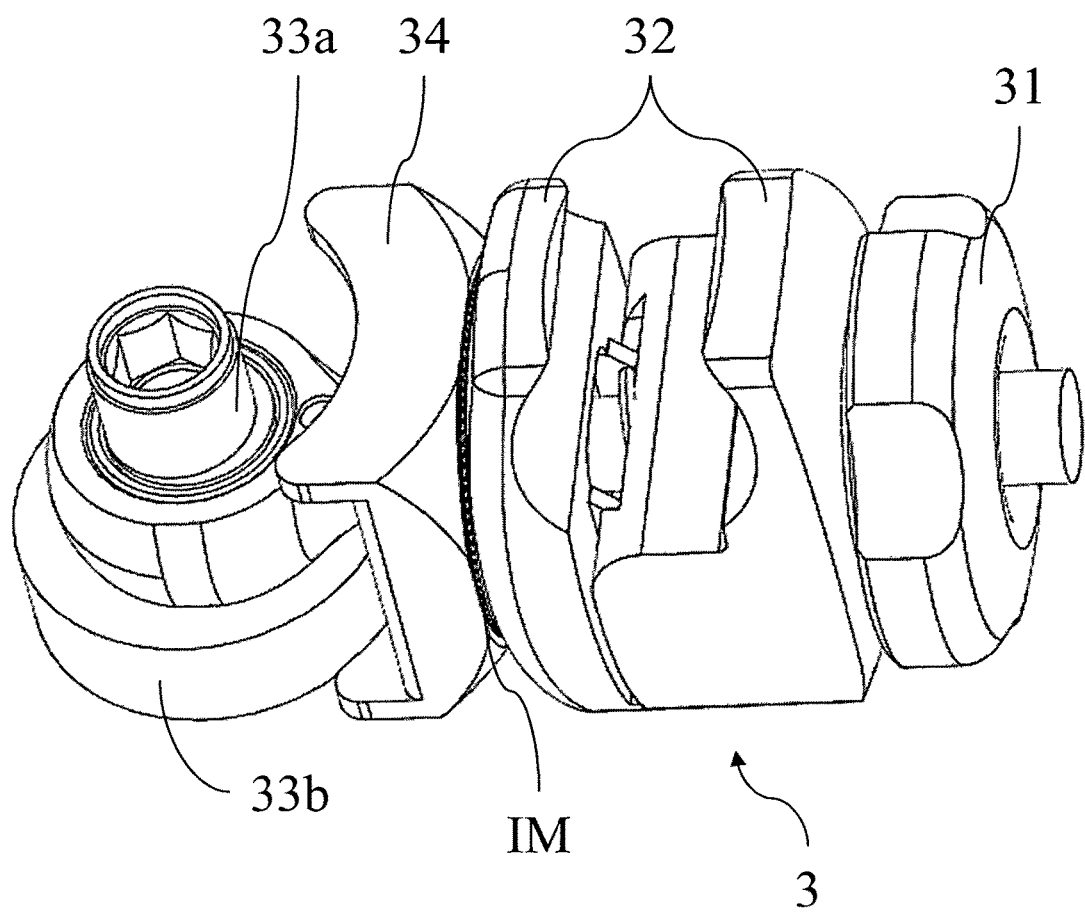
FIG. 12 shows a perspective view of the locking clamp of the anchoring group according to the present invention.

With reference to the attached figures, and in particular to FIGS. 1-4, the reference number 1 denotes overall an external fixator according to the present invention, designed in particular to be joined to a long bone of a patient using only unicortical pins or screws 100.

The external fixator comprises in particular a bar 2, known per se, which is fixed to the bone by means of two anchoring groups 20 respectively arranged in a distal position and proximal position.

Each of the anchoring groups 20 comprises two locking devices 10, each of which is designed to lock in position two unicortical pins 100 which are implanted in the bone of the patient. The two locking devices 10 extend laterally, in the manner of wings, from a central connecting body 11 of the anchoring group which also supports a locking clamp 3 designed to grip the bar of the external fixator 1.

In a preferred embodiment, shown in the present drawings, the locking devices 10 are made as modular elements which can be mounted separately on the connecting body 11; nevertheless, it is possible to envisage alternative embodiments in which the entire anchoring group 20 is formed as one piece, while retaining the particularly advantageous form and functional characteristics described below.

Figure 13:
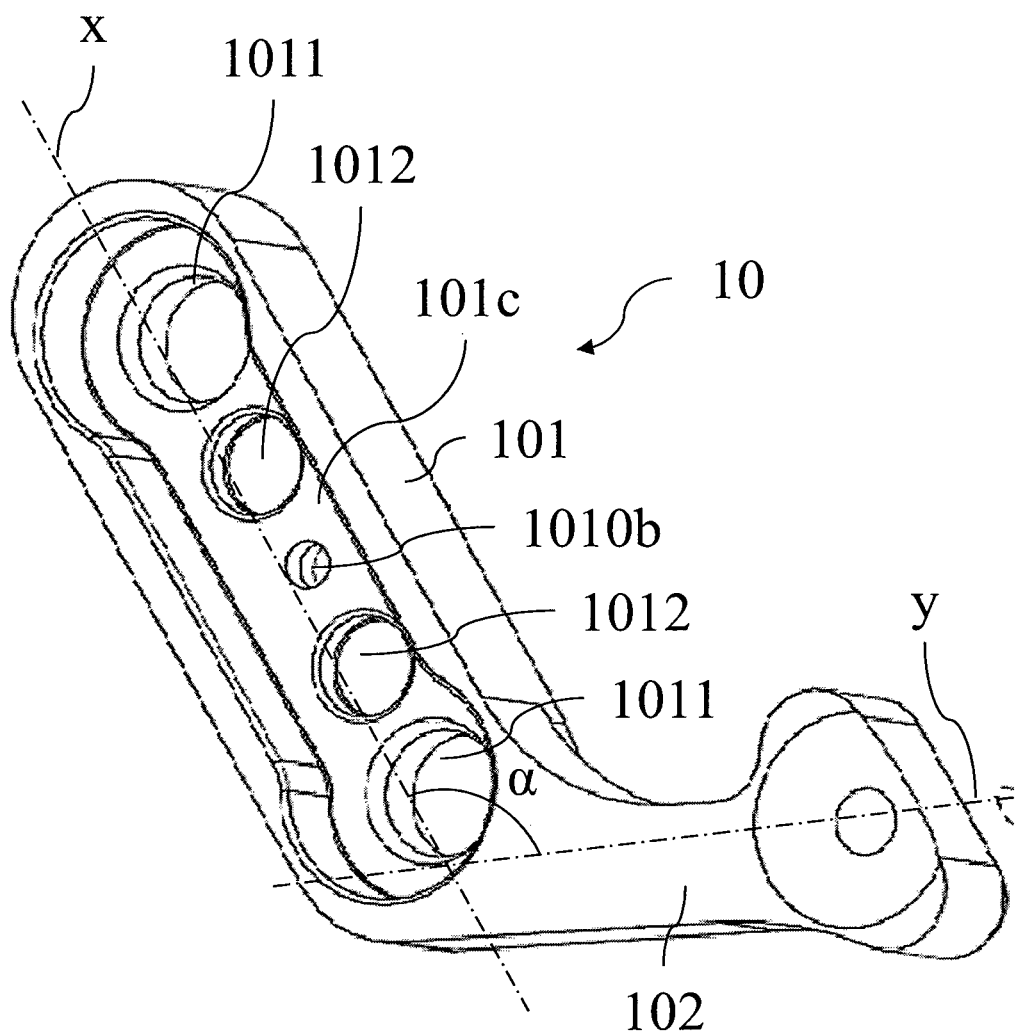
FIG. 13 shows a perspective view of the main body of a locking device according to the present invention.
Figure 14:
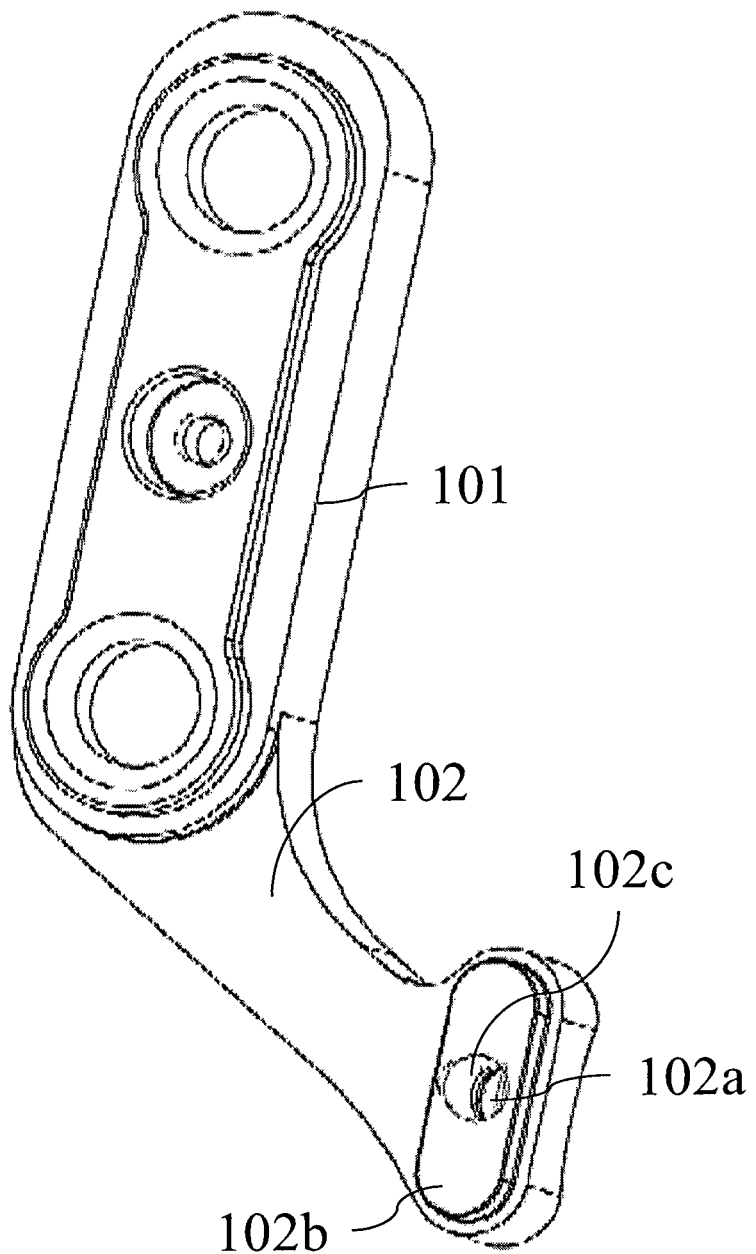
FIG. 14 shows another perspective view of the main body of FIG. 13.
Figure 15:
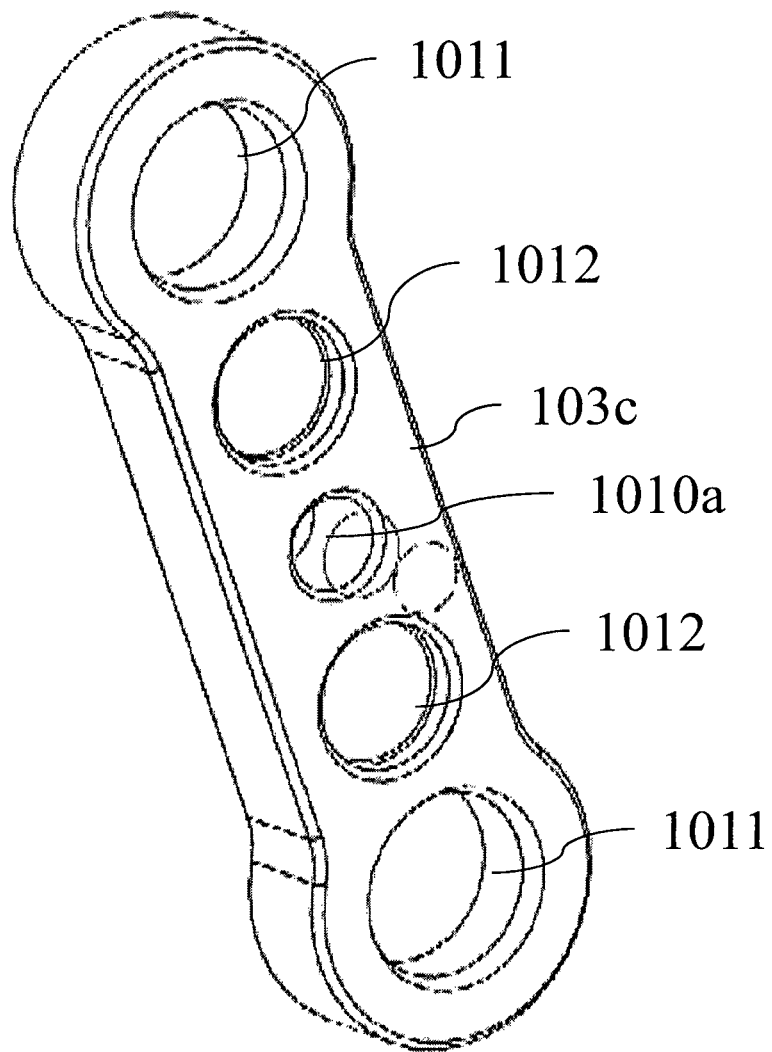
FIG. 15 shows a perspective view of the pressing body of the locking device of FIG. 13.
Figure 16:
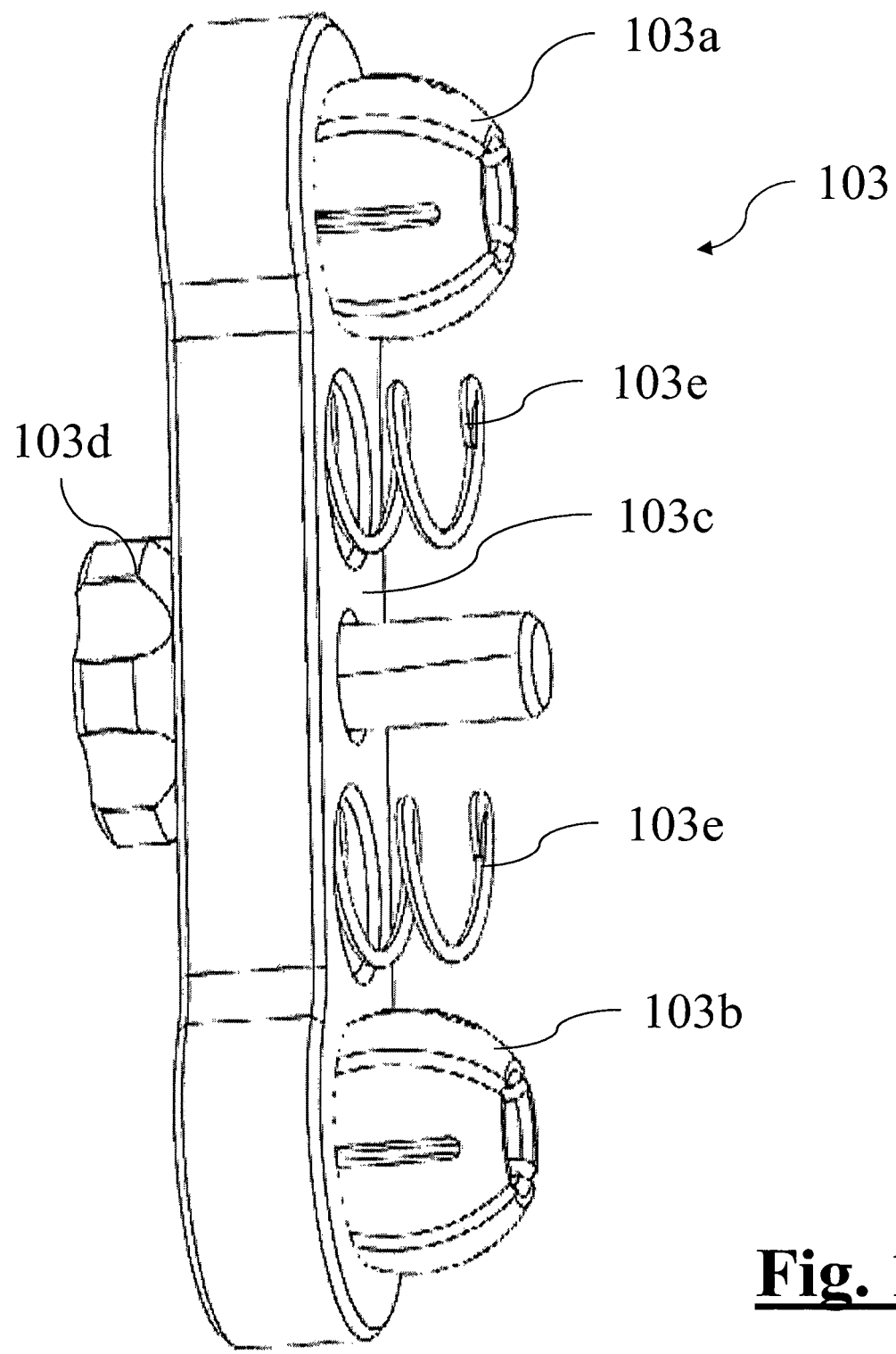
FIG. 16 shows a perspective view of the locking means of the locking device.

The single locking device 10 has a substantially L-shaped main body, namely a pin-locking arm 101 and a connection base 102 which together form an elbow. The angle a between the direction of extension of the arm x and the direction of extension of the base y, shown in FIG. 13, is preferably an angle that is substantially greater than a right angle, namely between 120° and 150°. It may be noted that the pin-locking arm 101 and the connection base 102 extend along a same plane of orientation $P_1$ of the locking device 10.

The pin-locking arm 101 has at its two opposite ends two seats 101a, 101b which are designed to lock a corresponding number of unicortical pins 100. This locking action is performed by the locking means 103 described below.

Figure 17:
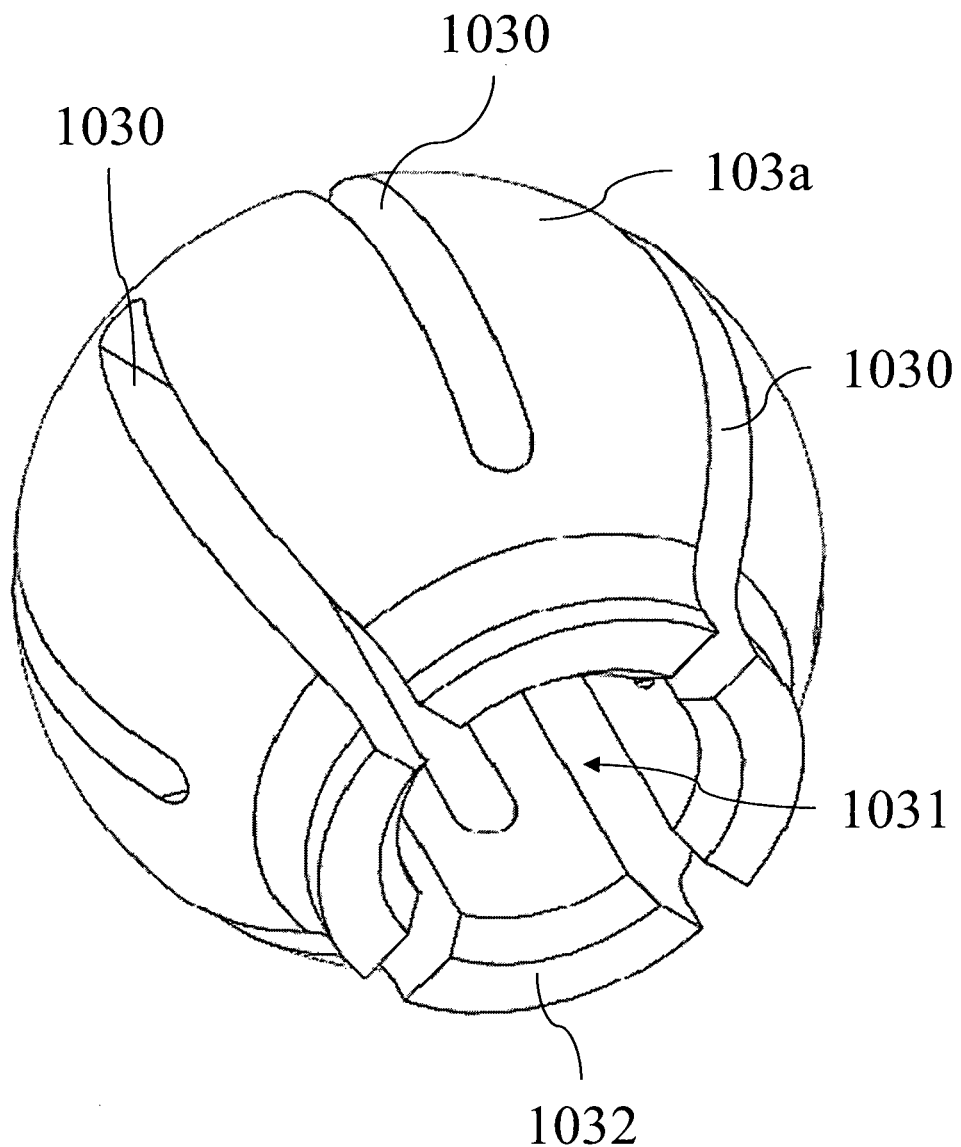
FIG. 17 shows a perspective view of a deformable sphere forming part of the locking means shown in FIG. 16.
Figure 18:
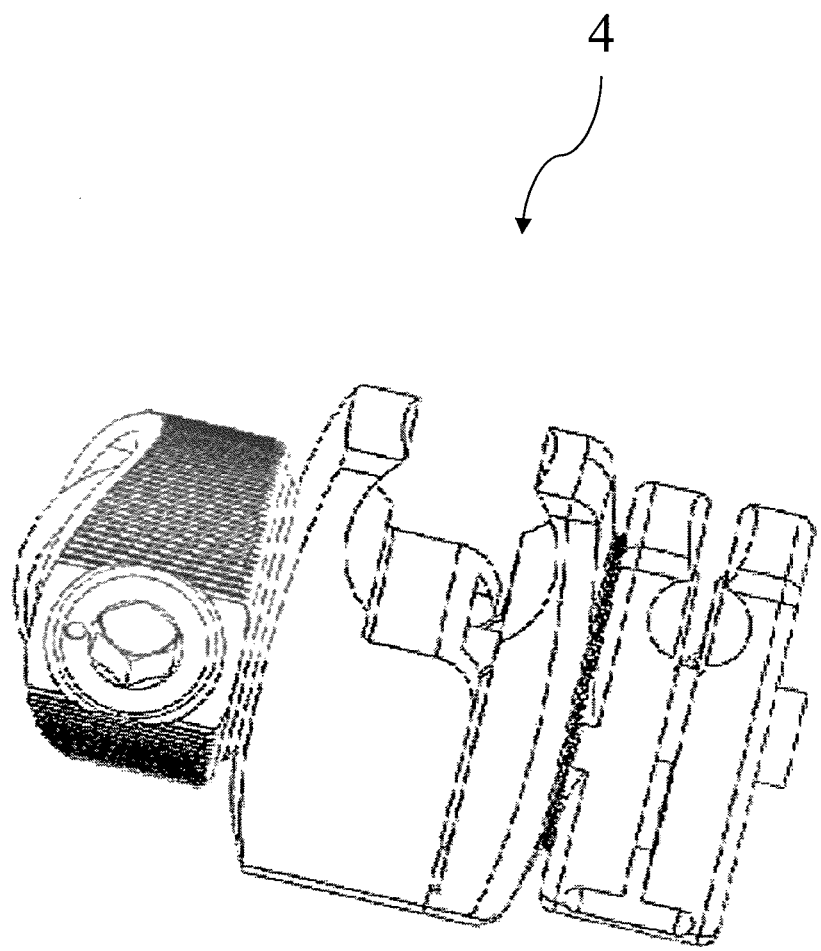
FIG. 18 shows a perspective view of a bar/pin clamp which can be associated with the connection bar of the external fixator according to the present invention.

The locking means 103 comprise, in particular, two deformable spheres 103a, 103b, one of which is shown separately in FIG. 17, which are provided with a diametral insertion channel 1031 that defines the actual seat 101a, 101b for the unicortical pins 100. The deformable spheres have a plurality of incisions that cross the sphere in a planar manner passing through the insertion channel 1031; the incisions lead alternately into one or the other of two opposite openings of the insertion channel 1031. Because of the incisions the sphere becomes deformed when it is compressed along the axis of the insertion channel, so that the insertion channel 1031 is constricted locally, by which the unicortical pin 100 housed therein will be locked.

The aforementioned deformable spheres 103a, 103b are housed between an elongated impression 101c, formed along the upper surface of the pin-locking arm 101, and a pressure plate 103c shaped to counter the opposite impression 101c. In particular, both the pressure plate 103c and the impression 101c have smooth through-holes 1011 at their ends; the two deformable spheres 103 are locked between two smooth through-holes 1011 situated opposite each other. The insertion channel 1031 of the spheres 103 is accessible via the smooth through-holes 1011 so as to allow the introduction of the unicortical pin 100.

The pressure plate 103c is connected to the impression via tightening means 103d which in particular take the form of a screw. The shank of the screw is inserted into a central through-hole 1010a of the pressure plate and then into an opposite central hole 1010b formed in the bottom of the impression 101c, on the outside of which it engages with a nut. Resilient setting means 103e are also arranged between the pressure plate 103c and the impression 101c, which are formed in particular by two helical springs that are compressed between the two elements and retained inside oppositely arranged depressions 1012 of the impression 101c and the pressure plate 103c.

The springs, arranged in an intermediate position between the deformable spheres 103 and the screw, oppose the tightening action of the latter, thus allowing the deformable spheres 103 to be deformed and the unicortical pins 100 to be locked inside them.

By driving the screw 103d, the pressure plate 103c simultaneously compress both the deformable spheres 103a, 103b locking in position the unicortical pins 100 inserted in the respective insertion channels 1031.

It should be noted that when the compression plate is not clamped, the deformable spheres 103 are rotatable inside their seat, such that the surgeon may modify as required the orientation of the inserted unicortical pins 100. Tightening the head of the screw 103d eliminates this degree of rotational freedom.

The deformable spheres 103 have, in one of the openings of the insertion channel 1031, a raised cylindrical edge 1032 which, once inserted inside the smooth through-hole 1011, limits the rotational movement of the element, while always allowing access to the insertion channel 1031.

In a preferred embodiment, the deformable spheres 103 allow the direction of the unicortical pins 100 to be varied with respect to the axis perpendicular to the plane of orientation $P_1$ by about 20°.

The connection base 102 has at its free end a fastening point 102a suitable for connection to the connecting body 11.

Moreover, the connecting body 11 has, on both sides, two alternative fastening seats 110a, 110b for the connection of the fastening point 102a.

The fastening point 102 of the locking device 10 presents an enlarged portion through which a fastening hole 102c passes and, on the opposite side of the enlarged portion, a projecting tenon 102b; on the other hand, the fastening seats 110a, 110b present a depression or mortise 110c shaped to match the tenon 102b, and a fastening hole 110d formed in the bottom of the mortise 110c.

When the tenon 102b is correctly inserted into the mortise 110c of one of the fastening seats 110a, 110b, the two fastening holes 102c, 110d are aligned so that a threaded connection element 104 that fixes the locking device 10 to the connecting body 11 may pass through them.

The connecting body 11 has a structure that is substantially symmetrical with respect to its median plane M. Said connecting body 11 has a cusp portion 111 at the front with opposite inclined surfaces that are symmetrical with respect to said median plane M, and at the rear a hinge portion 112, which will be described below.

Both the inclined surfaces of the cusp portion 111 have a top section with an inclination greater than the horizontal and a bottom section with a smaller inclination. The first fastening seat 110a is formed on the first section and the second fastening seat 110b is formed on the second section.

Thus, depending on whether the locking device 10 is connected to the first fastening seat 110a or to the second fastening seat 110b, two different inclinations of the plane of orientation $P_1$ with respect to the median-plane M can be obtained. Consequently, also the inclination of the preferential plane of orientation $P_2$ of the unicortical pins 100 is modified i.e. the plane on which the pins lie, with due allowance for any adjustments performed by means of the deformable spheres 103a, 103b.

The inclination imparted to the fastening seats 110a, 110b in the present invention is such that, by associating both locking devices 10 with the respective first seat 110a, an angle between the two planes of orientation $P_1$ is created that is smaller than a right angle; on the other hand, by associating the locking devices 10 with the second seat 110b, an angle between the two planes of orientation $P_1$ is obtained that is greater than a right angle. The first configuration is particularly suitable for small-size bones (for example ideal for tibial mounting), while the second configuration is suitable for large-size limbs (for example suitable for femoral mounting).

The hinge portion 112 of the connecting body 11 allows articulation, around an axis of rotation $r_1$ perpendicular to the median plane M, of a locking clamp 3.

The hinge portion 112 defines in particular a cylindrical seat 1120 intended to define interiorly an articulation hinge 33 of the locking clamp 3. A threaded element, with a shank which defines the pin 33a of the hinge 33 and a head which acts as a cover for the cylindrical seat 1120, is in fact screwed laterally into the cylindrical seat 1120. A shank 30 of the locking clamp 3, which comprises an eyelet end 30a which embraces the aforementioned pin 33a, is also inserted, via an upper groove 1121, inside the cylindrical seat 1120.

Outside of the cylindrical seat, the shank 30 passes through, in succession, an intermediate element 34, slidably movable along an outer cylindrical surface of the hinge portion 112, and two jaws 32 designed to grip in a known manner the bar 2 of the external fixator. A splined coupling IM is formed between the bottom jaw 32 and the intermediate element 34 that ensures restriction of rotation when the two parts are clamped against each other. The free end of the shank 30 is threaded and a lock nut 31 is screwed onto it.

When the abovementioned group is not clamped, adjustments both around the axis of rotation $r_1$ of the hinge and around the axis $r_2$ of the shank 30 are possible. Tightening the lock nut 31 causes the entire group to be pressed together and performs the triple function of locking the bar 2 between the jaws of the clamp 3 and blocking the two abovementioned rotational axes. In particular, the axis of rotation $r_1$ is blocked by the friction between the intermediate element 34 and the outer cylindrical surface of the hinge portion 112, and the axis of rotation $r_2$ is blocked by the locking action of the splined coupling IM.

Having described individually the single elements which make up the anchoring groups 20 of the external fixator 1, we shall now describe the different possibilities of assembling them in order to obtain different configurations of the said fixator.

First of all, it is pointed out that the locking devices 10 according to the present invention may be constructed in two configurations which are a mirror image of each other, namely a configuration oriented to the right of the connection base 102 and a configuration oriented to the left of the connection base 102.

The external fixator 1, which by nature is modular, comprises both right-hand and left-hand locking devices 10 which may be used alternatively by the surgeon in the field depending on the actual operating requirements.

Thus, depending on the locking devices chosen, each anchoring group 20 may be mounted in three different configurations: a U configuration, in which the two locking devices 10 are both oriented in the same direction, away from the locking clamp 3 of the anchoring group 20; an M configuration, in which the two locking devices 10 are both oriented in the direction of the locking clamp 3 of the anchoring group 20; and an S configuration, in which the locking devices 10 are oriented in opposite directions.

With reference to the enclosed figures: FIG. 1 shows an external fixator 1 in which both anchoring groups 20 have a U configuration; in FIG. 2 both anchoring groups 20 have an S configuration; in FIGS. 3 and 4 the proximal mounting group 20 has a U configuration and the distal group has an M configuration, i.e. in a position where the pin-locking arms 101 point in a distal direction and proximal direction, respectively.

The various configurations described above may be used alternatively by the surgeon, depending on the specific operating requirements and the morphology of the fractured bone. In particular, with the S configuration two unicortical pins 100 may be arranged in the vicinity of the fracture site, thereby increasing stability. It is a known fact that the relative spacing of the screws improves the stability of an external fixator 1.

In the case where additional stability is required, further unicortical pins 100 may be added, being directly fixed to the bar 2 by means of one or more bar/pin clamps 4 of the type known in the art.

A method for applying an external fixator 1 according to the present invention is described below, said method comprising the following steps:

preparing the first anchoring group 20, for example the distal anchoring group of the type described above, where necessary mounting it in the configuration most suitable for the intervention according to the modes described above;

inserting unicortical pins 100 in at least three of the seats 101a, 101b (but preferably all four of them) of the two pin-locking devices 101 of the anchoring group 20;

fixing the unicortical pins 100 to the long bone of the patient, rotating them by means of a special instrument, using the seats 101a, 101b as boring guides;

locking said unicortical pins 100 inside the seats 101a, 101b using the special locking means 103 described above.

It should be noted that before fixing the unicortical pins 100 to the bone, they may be oriented by rotating the deformable sphere 103a, 103b in which they are inserted and then locking them in position by tightening the aforementioned locking means 103.

It should in particular be noted how the unicortical pins have a self-tapping tip so that it is sufficient to rotate them by means of a light pressure, associating their head with a drilling device in order to create the fixation hole in the patient's bone, whereby said hole can only penetrate the first cortex.

The steps described above may then be repeated in order to fix a second anchoring group 20, for example the proximal anchoring group; following which, by performing the adjustments along the axes $r_1$ and $r_2$ of the locking clamps 3 of the two anchoring groups 20, they are aligned and connected to the bar 2.

As previously mentioned, in order to improve the stability of the external fixator, further unicortical pins 100, preferably two in number, may be used, associating them directly to the bar 2 by means of bar/pin clamps 4.

It should be noted that, during mounting of the anchoring groups, owing to the L-shaped form of the locking device 10, X-ray access to the bone site concerned in the intervention is never obstructed by the structure of the anchoring groups, so that the various parts which make up the group need not necessarily be made of radio transparent material.

It should also be noted that the non-invasive form of the anchoring group 20, in particular in its U configuration with the opening directed towards the bone end, allows easy access of an instrument for reaming the long bone of the patient and subsequently inserting an intramedullary nail, even when the anchoring group is positioned at the point where the nail end is inserted.

Obviously, a person skilled in the art, in order to satisfy any specific requirements which arise, may make numerous modifications and variations to the devices described above, all of which are however contained within the scope of protection of the invention, as defined by the following claims.

The invention claimed is:

1. An anchoring group for an external fixator, comprising:
    a connecting body crossed by a median plane defining a first side and a second side, the first side having at least a first and a second first side fastening seat, the second side having at least a first and a second second side fastening seat, said connecting body being designed to be coupled to an external fixator bar having a longitudinal axis lying on the median plane of the connecting body, wherein the connecting body has a cusp portion with opposite inclined surfaces symmetrical with respect to the median plane, said first and second side fastening seats being symmetrically formed on the opposite inclined surfaces of said cusp portion;
    a first locking device comprising at least one pin seat for locking first unicortical pins, said first locking device being alternatively coupled to either the first or the second first side fastening seat, the mounting of the first locking device on either the first or the second first side fastening seat determines either a first fixed inclination or a second fixed inclination of the first locking device with respect to the median plane of the connecting body;
    a second locking device comprising at least one auxiliary pin seat for locking second unicortical pins, said second locking device being alternatively coupled to either the first or the second second side fastening seat, the mounting of the second locking device on either the first or the second second side fastening seat determines either a first fixed inclination or a second fixed inclination of the second locking device with respect to the median plane of the connecting body;
    wherein the at least one auxiliary pin seat for locking second unicortical pins and the at least one pin seat for locking first unicortical pins not being aligned when the first locking device is mounted on either the first or the second first side fastening seat and the second locking device is mounted on either the first or the second second side fastening seat.

2. The anchoring group according to claim 1, wherein said first and second side fastening seats of the connecting body comprise a respective hole designed to be passed through by a threaded connection element and a respective depression intended to allow easy mating of a projecting of the locking devices.

3. The anchoring group according to claim 1, wherein said locking devices have two alternative right-handed and two alternative left-handed configurations which are a mirror image of each other, allowing for the formation of a plurality of alternative configurations of the anchoring group.

4. The anchoring group according to claim 1, wherein at least one of the locking device is formed as one piece with the connecting body.

5. The anchoring group according to claim 1, wherein at least one of the locking device is connected removably with at least one fastening seat of the connecting body.

6. The anchoring group according to claim 1, wherein the first and the second locking devices each comprises a respective pin-locking arm provided with seats suitable for the locking of the unicortical pins.

7. The anchoring group according to claim 6, wherein the two locking devices have their respective pin-locking arms oriented in opposite directions.

8. The anchoring group according to claim 6, wherein the two locking devices have their respective pin-locking arms both oriented in the direction of a locking clamp associated with the connecting body and designed to be coupled with a bar of an external fixator.

9. The anchoring group according to claim 8, wherein said locking clamp comprises a threaded shank and a locking nut which allow locking of two gripping jaws of the clamp, said threaded shank comprising an eyelet end which embraces a pin of an articulation hinge so as to allow locking of the articulation hinge simultaneously with the clamping of the gripping jaws.

10. The anchoring group according to claim 6, wherein the two locking devices have their respective pin-locking arms both oriented opposite the position of a locking clamp associated with the connecting body and designed to be coupled with a bar of an external fixator.

11. The anchoring group according to claim 1, further comprising a locking clamp designed to lock a bar of an external fixator in position, said locking clamp being coupled by means of an articulation hinge to the connecting body.

12. An external fixator for the fixation of long bones, comprising a distal anchoring group and a proximal anchoring group connected by a bar, at least one of the distal anchoring group and the proximal anchoring group being an anchoring group according to claim 1.

13. An anchoring group for an external fixator, comprising:
    a connecting body crossed by a median plane defining a first side and a second side, the first side having at least a first and a second first side fastening seat, the second side having at least a first and a second second side fastening seat, said connecting body being designed to be coupled to an external fixator bar having a longitudinal axis lying on the median plane of the connecting body;
    a first locking device comprising at least one pin seat for locking first unicortical pins, said first locking device being alternatively coupled to either the first or the second first side fastening seat, the mounting of the first locking device on either the first or the second first side fastening seat determines either a first fixed inclination or a second fixed inclination of the first locking device with respect to the median plane of the connecting body;
    a second locking device comprising at least one auxiliary pin seat for locking second unicortical pins said second locking device being alternatively coupled to either the first or the second second side fastening seat, the mounting of the second locking device on either the first or the second second side fastening seat determines either a first fixed inclination or a second fixed inclination of the second locking device with respect to the median plane of the connecting body;

wherein the at least one auxiliary pin seat for locking second unicortical pins and the at least one pin seat for locking first unicortical pins not being aligned when the first locking device is mounted on either the first or the second side fastening seat device is mounted on either the first or the second second side fastening seat;

wherein the first and the second locking devices each comprises a respective pin-locking arm provided with seats suitable for the locking of the unicortical pins;

wherein the respective pin-locking arms are both oriented in the direction of a locking clamp associated with the connecting body and designed to be coupled with a bar of an external fixator;

wherein the locking clamp comprises a threaded shank and a locking nut which allow locking of two gripping jaws of the clamp, said threaded shank comprising an eyelet end which embraces a pin of an articulation hinge so as to allow locking of the articulation hinge simultaneously with the clamping of the gripping jaws.

* * * * *